United States Patent [19]
Mendes et al.

[11] Patent Number: 6,102,955
[45] Date of Patent: Aug. 15, 2000

[54] SURGICAL METHOD, SURGICAL TOOL AND ARTIFICIAL IMPLANTS FOR REPAIRING KNEE JOINTS

[76] Inventors: David Mendes; Ruth Beer, both of Hoismans Kamil 46 Haifa, Haifa 34483, Israel

[21] Appl. No.: 09/039,476

[22] Filed: Mar. 16, 1998

Related U.S. Application Data

[63] Continuation-in-part of application No. 08/735,927, Oct. 24, 1996, Pat. No. 5,824,099, which is a continuation-in-part of application No. 08/375,085, Jan. 19, 1995, Pat. No. 5,580,353.

[51] Int. Cl.[7] .................................................. A61F 2/38
[52] U.S. Cl. ........................................................ 623/20
[58] Field of Search .............................. 623/19, 20, 18

[56] References Cited

U.S. PATENT DOCUMENTS

| | | | |
|---|---|---|---|
| 2,696,817 | 12/1954 | Prevo | 623/20 |
| 3,868,730 | 3/1975 | Kaufer et al. | 623/20 |
| 5,062,852 | 11/1991 | Dorr et al. | 623/20 |
| 5,071,438 | 12/1991 | Jones et al. | 623/20 |
| 5,116,375 | 5/1992 | Hofmann | 623/60 |
| 5,137,536 | 8/1992 | Koshino | 623/20 |
| 5,271,737 | 12/1993 | Baldwin et al. | 623/20 |
| 5,387,241 | 2/1995 | Hayes | 623/20 |
| 5,413,605 | 5/1995 | Ashby et al. | 623/20 |
| 5,554,192 | 9/1996 | Crowninshield | 623/20 |
| 5,658,341 | 8/1997 | Delfosse | 623/20 |
| 5,690,636 | 11/1997 | Wildgoose | 623/20 |

*Primary Examiner*—Paul J. Hirsch
*Attorney, Agent, or Firm*—Mark M. Friedman

[57] ABSTRACT

A surgical method and tool for reshaping a natural patella of the knee joint and fixing a patella implant to the remaining portion of the natural patella, an artificial patella implant, an artificial tibial knee component implant, and an artificial femoral knee component implant are disclosed.

5 Claims, 6 Drawing Sheets

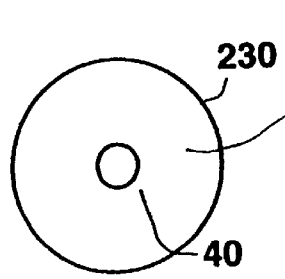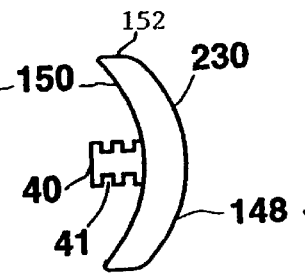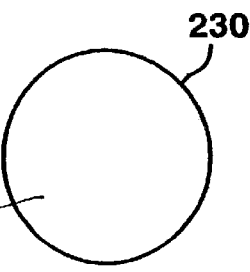
FIG. 4  FIG. 3  FIG. 5
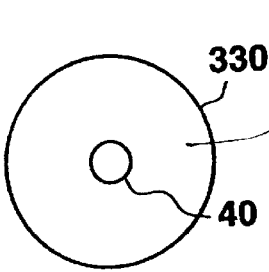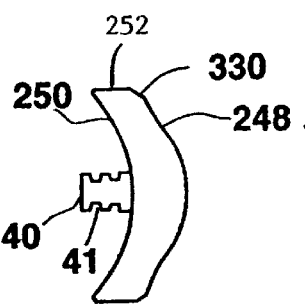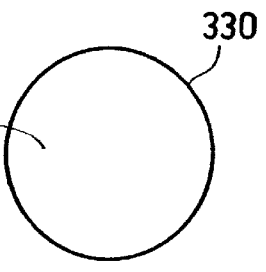
FIG. 7  FIG. 6  FIG. 8
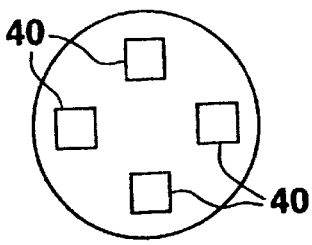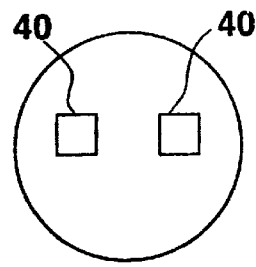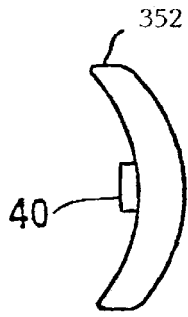
FIG. 10  FIG. 9  FIG. 11
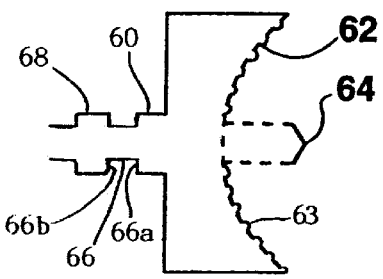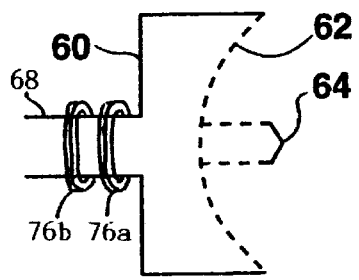
FIG. 12  FIG. 13

$\alpha = 5°$

SURGICAL METHOD, SURGICAL TOOL AND ARTIFICIAL IMPLANTS FOR REPAIRING KNEE JOINTS

This is a continuation-in-part of U.S. patent application Ser. No. 08/735,927, filed Oct. 24, 1996, now U.S. Pat. No. 5,824,099 which is a continuation-in-part of U.S. patent application Ser. No. 08/375,085, filed Jan. 19, 1995, now U.S. Pat. No. 5,580,353, issued Dec. 3, 1996.

FIELD AND BACKGROUND OF THE INVENTION

The present invention relates to a surgical method, a surgical tool and artificial implants for repairing knee joints. More particularly, the present invention relates to (i) a surgical method and tool for reshaping a natural patella of the knee joint and fixing a patella implant to the remaining portion of the natural patella, (ii) an artificial tibial knee component implant, (iii) an artificial femoral knee component implant, and (iv) a patella implant.

Joint replacement is becoming increasingly widespread. One of the most widely practiced joint replacement involves the knee joint. In many cases, the replacement of the knee joint with a prosthesis or artificial implant also involves the replacement of a portion of the patella with a prosthetic.

Partial replacement of the patella is widely used in the surgical replacement of a damaged portion of the knee joint. However, it is known that, in a significant percentage of the cases, the patella implant typically fails after five to fifteen years.

One of the typically occurring failures is near or at the periphery of the circular or elliptical patella implant, where the thickness of the patella implant material, typically high molecular weight high density polyethylene (HDPE), is at its smallest.

A failing patella could lead to significant pain in the patient and typically requires a second operation to replace the failed patella implant and often the entire prosthetic joint.

U.S. Pat. No. 5,580,353 discloses a prosthetic patella implant adapted to substantially structurally fit a remaining portion of the natural patella with maximal preserving of healthy natural tissue and minimal wear of the implant.

U.S. patent application Ser. No. 08/735,927 now U.S. Pat. No. 5,824,099 discloses a surgical method and tool for preparing a natural patella by removing a portion thereof to accept the patella implant described in U.S. Pat. No. 5,580,353.

In one aspect, like U.S. Pat. No. 5,580,353 and U.S. patent application Ser. No. 08/735,927, now U.S. Pat. No. 5,824,099 the present invention concerns a prosthetic patella implant adapted to substantially structurally fit a remaining portion of the natural patella with maximal preserving of healthy natural tissue and minimal wear of the implant and a surgical method and tool for preparing a natural patella by removing a portion thereof to accept the patella implant.

U.S. Pat. Nos. 4,550,448; 4,653,488; 4,298,992; 4,834,756; 4,944,756; 5,035,700 and 5,192,324, which are incorporated by reference as if fully set forth herein, disclose artificial tibial knee component implants to be used, for example, as the tibial knee component in total knee joint implants.

These implants are provided with cylindrical, rectangular or T shaped in cross section stems implantable into a cut formed into a tibia bone.

As such, these implants suffer disadvantages in engaging and in harmonically functioning with the reshaped tibial bone as further detailed below.

Thus, in another aspect, the present invention concerns improvements to the tibial knee component implant stem.

U.S. Pat. Nos. 4,298,992, 4,950,298; 5,047,058; 5,053,037; 5,100,408; 5,282,803; 5,514,140; 5,354,075; 5,417,694 and 5,549,688; UK Pat. No. 2067412 and AU Pat. No. 542787, which are incorporated by reference as if fully set forth herein, disclose artificial femoral knee component implants to be used, for example, as the femoral knee component in total knee joint implants.

These implants are provided with a substantially linear groove which is expected to simulate the trochlear groove of a natural femur bone and which is expected to serve, when implanted, as a guiding route for the patella (or patella implant) with respect to the femoral implant.

Featuring a linear groove, these femoral implants suffer disadvantages in simulating the natural relative knee components movement, wherein in the natural case the patella follows helicoid (sinuous) course with respect to the femur bone.

Therefore, in another aspect, the present invention concerns improvements to the shape of a femoral knee component implant, so as to allow for better simulation of the natural knee movement.

SUMMARY OF THE INVENTION

According to the present invention there are provided (i) a surgical method and tool for reshaping a natural patella of the knee joint and fixing a patella implant to the remaining portion of the natural patella, (ii) an artificial tibial knee component implant, (iii) an artificial femoral knee component implant, and (iv) a patella implant.

Thus, according to further features in preferred embodiments of the invention described below, provided is a patella implant adapted to substantially structurally fit a remaining part of a natural patella with maximal reserving of healthy natural tissue and minimal wear of the implant, comprising (a) a non-planar and protruding upper surface for sliding over a femoral articulating member; (b) a non-planar and recessed undersurface for fixation to a non-planarly and protruding sectioned natural patella; and (c) a circumferential facet therebetween. Some additional features of the patella implant are described in U.S. Pat. No. 5,580,353, which is incorporated by reference as if fully set forth herein.

As used herein in the specification and claims below, the term "about" refers to ±10%.

According to further features in preferred embodiments of the invention described below, provided is a method of repairing a natural patella, comprising the steps of (a) preparing a natural patella by removing a portion thereof so as to leave a non-planar and protruding remaining portion; and (b) fixing a patella implant onto the non-planar and protruding remaining portion of the natural patella, the patella implant including (i) an upper surface being adapted for sliding over a femoral articulating member; (ii) a substantially non-planar and recessed undersurface for fixation to the non-planar and protruding remaining portion of the natural patella; and (iii) a circumferential facet.

According to still further features in the described preferred embodiments the remaining portion of the natural patella is substantially convex.

According to still further features in the described preferred embodiments the remaining portion of the natural patella is formed with grooves or pits.

According to still further features in the described preferred embodiments the remaining portion of the natural patella includes a plurality of planes.

According to still further features in the described preferred embodiments the patella implant includes at least one peg connected to or integrally formed with the undersurface.

According to still further features in the described preferred embodiments the method further comprising the step of drilling at least one hole within the remaining portion of the natural patella for accepting the at least one peg.

According to still further features in the described preferred embodiments the drilling of the hole is carried out simultaneously with the preparation of the natural patella by means of a reamer, the reamer including (a) a non-planar and recessed rotatable reaming member, the recessivity of the reaming member being substantially matching to the recessivity of the undersurface of the patella implant; and (b) a bit protruding from the concave reaming member for drilling a hole in the natural patella, the bit guiding the rotatable reaming member to a predetermined portion of the natural patella.

According to still further features in the described preferred embodiments the diameter of the patella implant substantially equals the diameter of the natural patella.

According to still further features in the described preferred embodiments the diameter of the patella implant is smaller than the diameter of the natural patella.

According to still further features in the described preferred embodiments the circumferential facet is cylindrical.

According to still further features in the described preferred embodiments the circumferential facet is conical.

According to still further features in the described preferred embodiments the patella implant partially intrudes into the remaining portion of the natural patella.

According to still further features in the described preferred embodiments the preparation of the natural patella is carried out using a reamer, the reamer including a non-planar and recessed rotatable reaming member, the recessivity of the reaming member substantially matches the recessivity of the undersurface of the patella implant.

According to still further features in the described preferred embodiments the preparation of the natural patella is preceded by drilling a hole within the natural patella, and wherein the reaming member includes a bit having a blunt end for guiding the reaming member through the hole.

According to further features in preferred embodiments of the invention described below, provided is a reamer for use in preparing a natural patella to accept a patella implant having a non-planar and recessed undersurface, comprising a non-planar and recessed rotatable reaming member, the recessivity of the rotatable reaming member being substantially matching to the recessivity of the undersurface, the rotatable reaming member including a substantially solid bit protruding therefrom.

According to still further features in the described preferred embodiments the bit features a sharp (e.g., pointed) tip for drilling a hole in the natural patella.

According to still further features in the described preferred embodiments the bit features a substantially blunt tip for guiding the reaming member through a hole pre-drilled in the natural patella.

According to still further features in the described preferred embodiments the diameter of the reaming member substantially equals the diameter of the natural patella, the natural patella having a diameter of between about 28 millimeters and about 44 millimeters.

According to still further features in the described preferred embodiments the diameter of the reaming member is smaller than the diameter of the natural patella, the natural patella having a diameter of between about 28 millimeters and about 44 millimeters.

According to still further features in the described preferred embodiments the reamer further comprising a shaft member, the shaft member featuring a circumferential depression for accepting an external rod therein, the rod being connected to an external guiding device.

According to still further features in the described preferred embodiments the reamer further comprising a shaft member, the shaft member featuring two spaced circumferential extensions for accepting an external rod between the extensions, the rod being connected to an external guiding device.

According to still further features in the described preferred embodiments at least one of the circumferential extensions is movable along the shaft member.

Thus, according to the present invention there is provided a design which will enable the manufacture of a HDPE patella implant with an overall thickness of not less than about 6 or 8 millimeters. However, if a ceramic or composite material patella implant is of choice, than the overall thickness of the patella may be reduced to, for example, not less than about 2–3 millimeters, since these materials are more resilient than HDPE.

This thickness is considered in the scientific literature as an optimal thickness for a high molecular weight high density polyethylene (HDPE) patella implant for use in an average person weighing 60–70 kg or more, for preventing high stresses within the material. Smaller thicknesses are to be used in smaller patients.

The use of the augmented minimum thickness eliminates one of the main causes of failure of patella implants and enhances the durability of the implant.

To provide the required optimal thickness of the patella implant, the natural patella is cut, reamed and trimmed in such a manner as to remove a total of up to about 8 millimeters or more from the natural bone and cartilage to leave a convex shape which complements the concave shape of the undersurface of the patella implant.

The concave undersurface of the patella implant substantially fits the appropriately reamed remaining portion of the natural patella. The upper surface articulates with the articulating femoral member, typically a groove, and is shaped to substantially fit the corresponding articulating portion of the femoral component of the total knee implant. When the articulating femoral member is a groove, the upper surface of the patella implant is typically substantially convex. Where the upper surface is convex the convexity of the upper surface and the concavity of the undersurface of a patella implant according to the present invention do not necessarily conform to each other and may be independently varied to accommodate the specific design of the femoral groove and the femoral condyles, or their equivalent, and the convexity of the prepared natural patella.

The present invention successfully addresses the shortcomings of the presently known configurations by providing a surgical method and tool for repairing a natural patella by reshaping the natural patella and fixing a patella implant to the remaining portion of the natural patella, such that the overall combination of patella implant and remaining natural patella features a maximal biomechanical stability.

This is achieved by maximizing the volume of the remaining natural patella, minimizing the potential damage to necessary blood vessels at the periphery of the natural patella, conferring an optimal mechanical stability to the implant itself by limiting its minimal thickness to about 8 millimeters or alternatively about 6 millimeters, and providing complementary shapes to the implant and the remaining natural tissue.

According to another embodiment of the present invention provided is a tibial prosthetic component to be used in partial or total knee replacement procedure comprising a tibial end-like part and an anchoring stem having a proximal end being connected to or integrally formed with the tibial end-like part, the anchoring stem further having a distal end, the anchoring stem featuring three longitudinal extensions extending substantially from the proximal end to substantially the distal end, the three longitudinal extensions forming angles therebetween in a range of 105°–150°, such that, when the stem is inserted into a cut in a reshaped tibial bone of a patient, at least two of the three longitudinal extensions are positioned closer to a compact wall of the tibial bone, thereby load transfer between the tibial prosthetic component and the tibia is improved.

According to still further features in the described preferred embodiments each of the angles is of about 120°, thereby substantially forming a clover leaf shape in cross section.

According to still further features in the described preferred embodiments the stem is about 2.5–3.0 times thinner at the distal end as compared with the proximal end.

According to still further features in the described preferred embodiments ends of the at least two of the three longitudinal extensions are about 40 millimeters apart.

According to still further features in the described preferred embodiments the tibial end-like part includes a plastic upper plate and a metal back. Alternatively, the tibial end-like part is made of plastic.

Thus, the present invention further successfully addresses the shortcomings of the presently known configurations by providing tibial prosthetic component to be used in partial or total knee replacement procedure comprising a tibial end-like part and an anchoring stem featuring a clover leaf cross section, thereby improving load transfer from the tibial prosthetic component to the circumferential compact bone of the tibia.

According to another embodiment of the present invention there is provided a femoral prosthetic component to be used in partial or total knee replacement procedure comprising a femoral end-like part being formed with lateral and medial elevations simulating lateral and medial condyles of a natural femur, the elevations forming an interelevations groove therebetween, the interelevations groove simulating a natural intercondylar groove of the natural femur, the femoral end-like part being further formed with a helicoid groove simulating a natural trochlear grove of the natural femur, the helicoid groove being located in an anterior aspect of the femoral end-like part and terminating where the interelevations groove originating, such that when the femoral prosthetic component is implanted in a patient, the helicoid groove dictates a patella or a patella implant of the patient to follow a helicoid route.

According to still further features in the described preferred embodiments the helicoid groove features a raised lateral wall.

According to still further features in the described preferred embodiments the helicoid groove dictates a proximal—lateral to distal medial helicoid route for the patella or patella implant.

According to still further features in the described preferred embodiments the helicoid groove is 60±15 millimeters in length.

According to still further features in the described preferred embodiments the helicoid groove is 30±10 millimeters in width.

According to still further features in the described preferred embodiments the helicoid groove is 5±3 millimeters in depth.

According to still further features in the described preferred embodiments the femoral prosthetic component further comprising an anchoring stem having a proximal end being connected to or integrally formed with the femoral end-like part.

According to still further features in the described preferred embodiments the femoral end-like part is made of metal.

Thus, the present invention further successfully addresses the shortcomings of the presently known configurations by providing a femoral implant component designed to approximately simulate the anatomical shape of the femoral part of the knee joint.

BRIEF DESCRIPTION. OF THE DRAWINGS

The invention is herein described, by way of example only, with reference to the accompanying drawings, wherein:

FIG. 3 is a cross sectional view of one embodiment of a patella implant according to the present invention;

FIG. 4 is a back view of the patella implant of FIG. 3;

FIG. 5 is a front view of the patella implant of FIG. 3;

FIG. 6 is a cross sectional view of another embodiment of a patella implant according to the present invention;

FIG. 7 is a back view of the patella implant of FIG. 6;

FIG. 8 is a front view of the patella implant of FIG. 6;

FIG. 9 is a back view of the patella implant showing a pair of fixation members;

FIG. 10 is a back view of the patella implant showing four fixation members;

FIG. 11 is a cross sectional view of another embodiment of a patella implant according to the present invention;

FIG. 12 is a cross sectional view of one embodiment of a reamer which may be used to prepare a natural patella for acceptance of a patella implant according to the present invention;

FIG. 13 is a side view, partially in cross section, of a second embodiment of a reamer according to the present invention.

Figure 18:
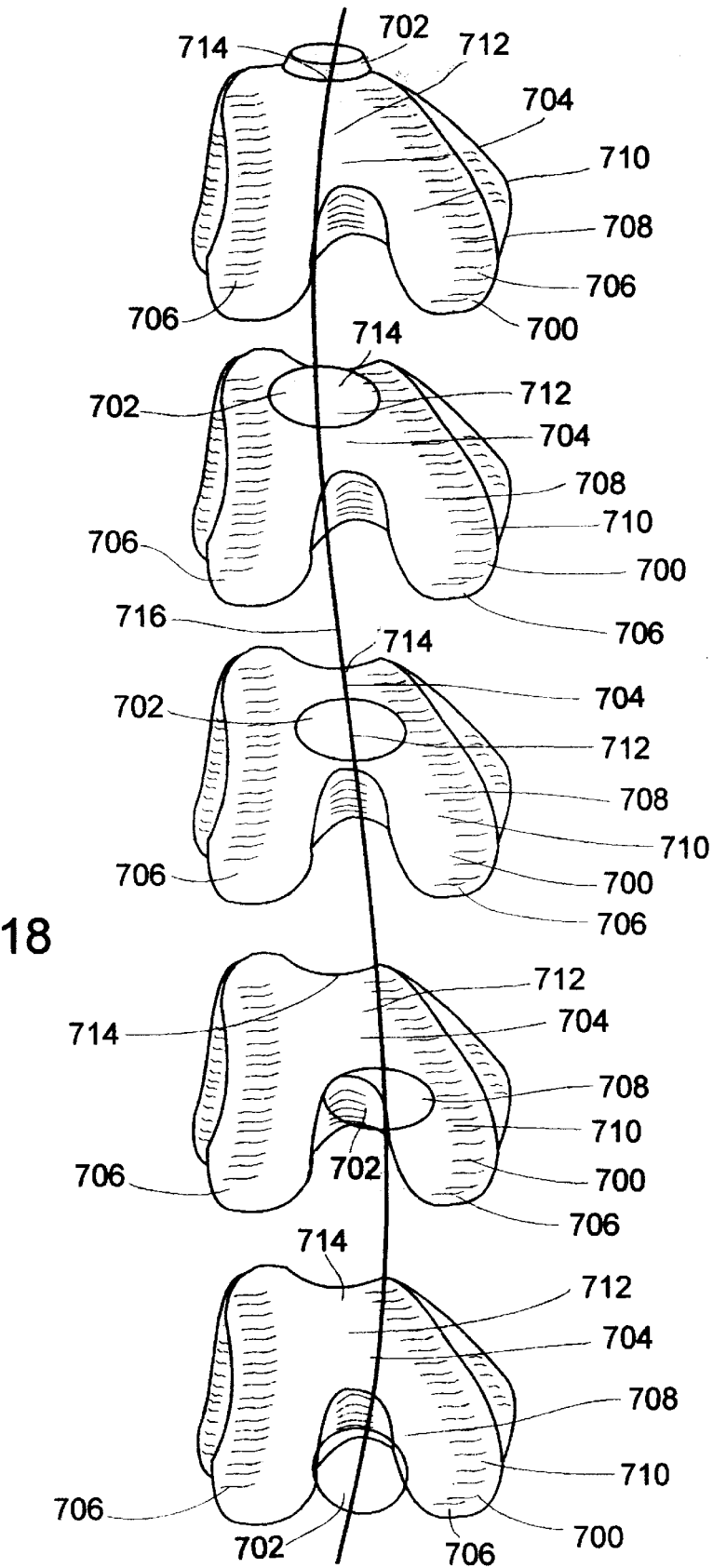
Figure 19:
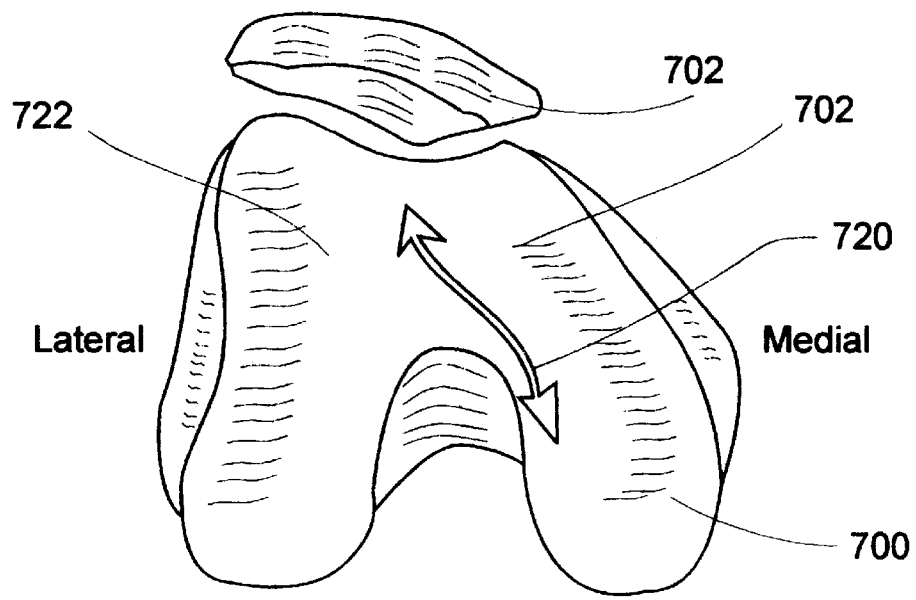
Figure 20:
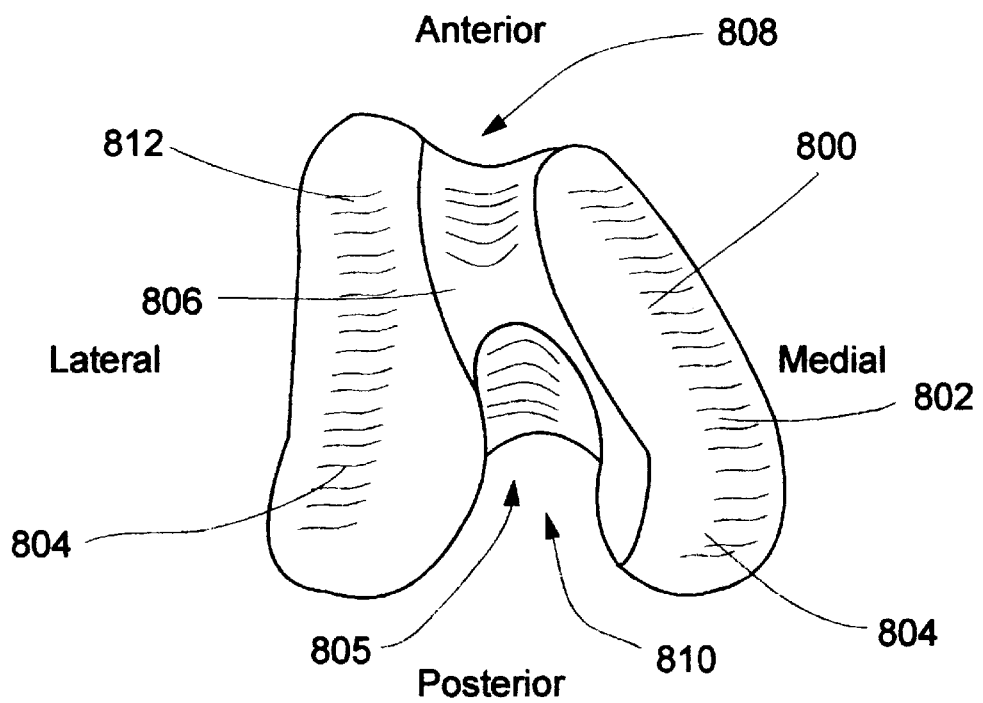

FIG. 18 demonstrates the helicoid relative movement between the patella and the femur during knee flexion;

FIG. 19 demonstrates the relative positions of the patella and the femur while the knee is fully extended; and FIG. 20 is a perspective view of a femoral implant according to the present invention.

DESCRIPTION OF THE PREFERRED EMBODIMENTS

The present invention is of a surgical method, a surgical tool and artificial implants which can be used for repairing knee joints. Specifically, the present invention provides (i) a surgical method and tool for reshaping a natural patella of the knee joint and fixing a patella implant to the remaining portion of a natural patella, (ii) an artificial tibial knee component implant having a stem shape which enables better anchorage and communication with a reshape tibial bone, (iii) an artificial femoral knee component implant which enables better simulation of a natural knee movement, and (iv) a patella implant.

The principles and operation of the surgical method, tool and artificial implants according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
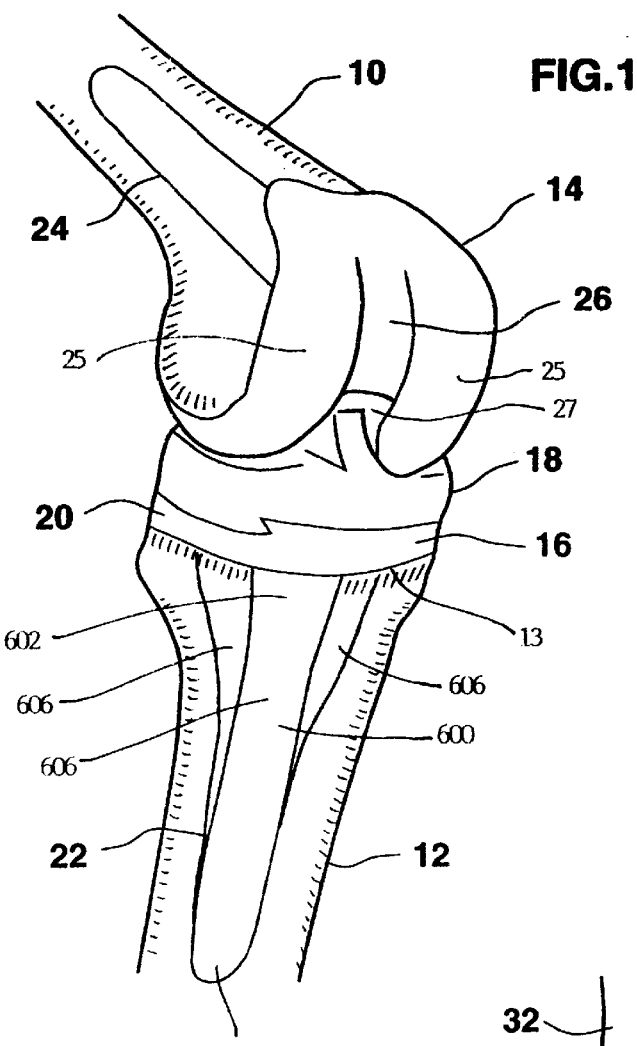
FIG. 1 is perspective view of a typical artificial knee joint.

Referring now to the drawings, FIG. 1 illustrates a typical knee joint prosthesis. The knee joint is formed between the lower end of the femur 10 and the upper end of the tibia 12. In a total knee replacement, the lower end of femur 10 is replaced with a femoral prosthetic component 14 while the upper end of tibia 12 is replaced with a tibial prosthetic component 16. To this end, both the tibia and femur are suitably reshaped to accept components 14 and 16. In particular, the tibia is reshaped to have a planar surface 13 (best emphasized in FIG. 2) which supports component 12.

Tibial prosthetic component 16 is typically made up of a plastic upper plate 18 and a metal back 20 which together form a tibial end-like part. Bone cement and a tibial anchorage stem 22 connected to or integrally formed with metal plate IS are typically used to anchor tibial prosthetic component 16 onto reshaped tibia 12. Tibial anchorage stem 22 may feature various lengths, widths and shapes, as further detailed hereinunder.

Femoral prosthetic component 14 is typically made of metal and is anchored into femur 10, preferably with a femoral anchorage stem 24. The face of femoral prosthetic component 14 which contacts tibial prosthetic component 16 is typically shaped to simulate the natural knee to include condyle-like elevations 25 and grooves 26 and 27 therebetween, which function similar to the natural trochlear groove and the intercondylar groove, respectively. It is on groove 26, or its equivalent, that the patella slides, as can be best be seen in FIG. 2.

Figure 2:
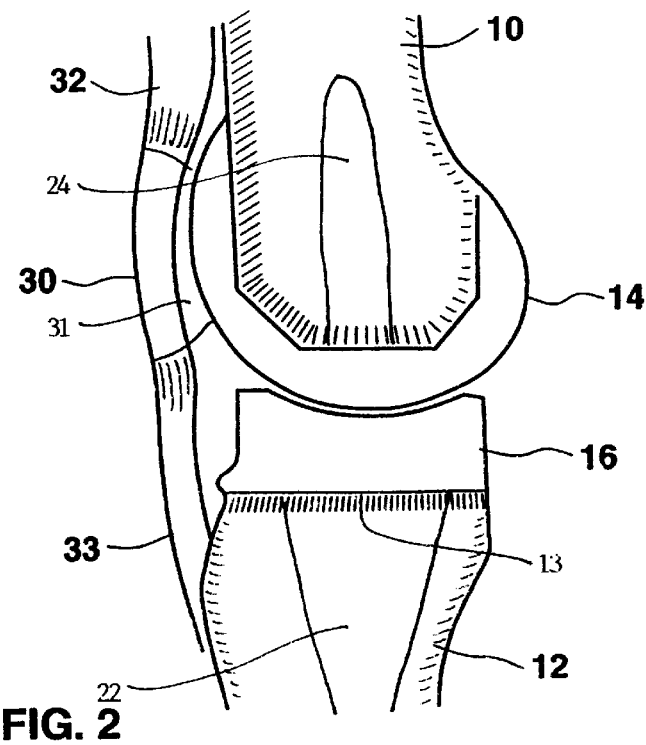
FIG. 2 is a side view of the artificial knee joint as in FIG. 1 showing, the patella, quadriceps tendon and patella tendon.

FIG. 2 illustrates a total knee implant including the replacement 31 of the articulating portion (the portion facing the knee) of the patella. The patella (knee cap) 30 is a disc-shaped member which is connected to the quadriceps tendon 32 and to the patella tendon 33 and is slidable over the lower end of femur 10. The portion of patella 30 facing the knee (patella implant 31) is typically, but not necessarily, convex and is dimensioned to slidably engage the corresponding portion of femoral prosthetic component 14, typically condyles 25 and groove 26 (FIG. 1), which simulates the trochlear groove as further detailed below. Please note that groove 26 in FIG. 1 has a linear geometry which is the prevalent groove shape in prior art femoral implants.

The portion of patella 30 away from the knee (the remaining natural patella) is connected to quadriceps tendon 32 and patella tendon 33. Quadriceps tendon 32 is connected to the quadriceps muscle which is, in turn, attached to femur 10. Patella tendon 33 is connected to tibia 12. In this way patella 30 slides over the knee joint during flexion and extension of the joint. The presence of patella 30 facilitates the sliding of quadriceps tendon 32 and further enhances its mechanical efficiency.

To surgically repair a damaged patella what is done is to remove a portion of the articulating surface (the surface facing the knee joint) of the natural patella, leaving the connection between the natural patella and the muscle intact.

Once a portion of the patella has been removed, a prosthetic, or implant, may be fixed to the remaining portion of the natural patella by some suitable means. The implant is shaped to substantially slidably fit within the groove, or its equivalent, of the corresponding natural or prosthetic lower end of the femur, depending on whether the natural lower femur is to remain or be replaced, respectively. Attachment of the implant to the natural patella may be effected with adhesives, cements or other bonding materials and/or through use of pegs, as described in more detail below.

U.S. patent application Ser. No. 08/375,085 discloses a prosthetic patella implant adapted to substantially structurally fit a remaining portion of the natural patella with maximal preserving of healthy natural tissue and minimal wear of the implant.

As shown in FIGS. 3–8, the patella implant, 230 or 330 features a non-planar and protruding upper surface 148 or 248, e.g., convex or substantially convex, respectively, adapted for sliding over a femoral articulating member. The patella implant, 230 or 330, further features a substantially non-planar and recessed, e.g., concave, undersurface, 150 or 250, for fixation to a non-planarly and protruding, e.g., convexly or substantially convexly, sectioned natural patella. The patella implant, 230 or 330 further features a circumferential facet, 152 or 252.

When using a polyethylene patella implant, the distance between upper surface 148 or 248 and the undersurface 150 or 250 is at least about 8 millimeters, or at least about 6 millimeters for small patients, so as to confer maximal mechanical integrity to the patella implant. However, if a ceramic or composite material patella implant is of choice, the distance between upper surface 148 or 248 and the undersurface 150 or 250 is at least about 2–3 millimeters.

Undersurface, 150 or 250, preferably features a recessed shape so as to allow maximal preserving of remaining natural bone tissue. Undersurface, 150 or 250, may therefore be concave, may feature a flattened central portion or have any other recessed shape which enhances the bonding of the implant to the natural patella. For example, undersurface, 150 or 250, may further feature a spiral groove or a plurality of concentric grooves to enhance bonding. There is no limitation to the design of undersurface, 150 or 250 since in many cases patella implant 230 or 330 is manufactured by molding.

Circumferential facet, 152 or 252, is specifically designed so as to minimize potential damage to necessary blood vessels at the periphery of the natural patella. As shown in FIGS. 3 and 6, circumferential facet, 152 or 252, may feature a cylindrical shape. However, as shown in FIG. 11, circumferential facet may feature a conical shape 352.

Figure 15:
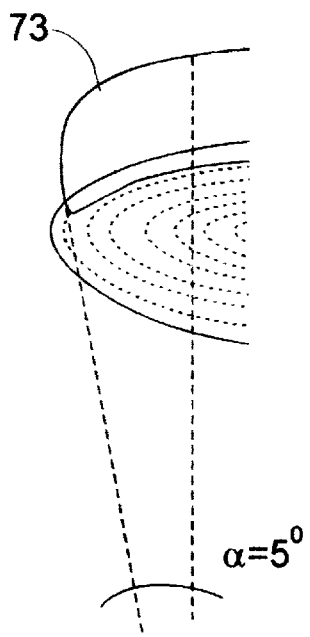
FIGS. 15 and 16 illustrate another embodiment of a method according to the present invention.
Figure 16:
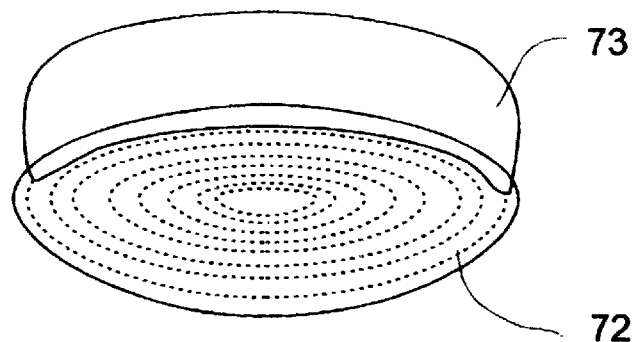

A conical circumferential facet may be used for facilitating the attachment of the patella implant to the remaining portion of the natural patella by means of press fitting or other fixation techniques (FIGS. 15 and 16).

According to any of the patella implant embodiments according to the present invention, the edges of the implant are contoured.

As shown in FIGS. 3–11, the patella implant may include one or more pegs 40. Pegs 40 may be of any suitable size. Thus, pegs 40 may extend beyond the lower edge of the circumferential facet (FIGS. 3 and 6). Alternatively, pegs 40 may not extend beyond the lower edge of the circumferential facet (FIG. 11). Each of pegs 40 is connected to or integrally formed with the patella implant.

Preferably, pegs 40 are formed with circumferential depressions 41 (FIGS. 3 and 6) which improve the bonding and anchorage of the patella implant to the natural bone tissue by providing enhanced friction and further providing space in which cement and the like can accumulate.

The present invention provides a surgical method for repairing a natural patella by reshaping the natural patella and fixing a patella implant to the remaining portion of the natural patella, such that the fixation between the remaining part of the natural patella and the implant is improved and the overall combination of the patella implant and the remaining natural tissue has maximal biomechanical stability, as compared with the prior art.

Furthermore, the present invention provides a surgical tool for preparing a remaining natural patella to accept the patella implant.

A method according to the present invention includes the step of preparing a natural patella to accept a patella implant having a non-planar recessed, e.g., substantially concave, undersurface, such that there is maximal preservation of natural bone tissue and minimal damage to important blood vessels at the periphery of the natural patella.

Thus, the natural patella is surgically prepared to preferably adopt a non-planar and protruding, e.g., convex, substantially convex or pyramid-like, shape which substantially matches in size and shape to be accepted by the undersurface of the patella implant.

The patella may be reshaped to include spiral grooves, concentric grooves pits, or any other surface irregularity, providing enhanced friction and further providing space in which cement and the like can accumulate and enhance fixation and stability.

A method according to the present invention may further include the step of drilling at least one hole within the remaining portion of the natural patella for accepting at least one peg, as shown in FIGS. 3–11, which is connected to the patella implant.

The surgical preparation of the natural patella is preferably carried out using a special surgical tool which cuts the bony patella to precisely the desired shape with minimal interference of its blood supply from the surrounding tissues by preservation of the peripheral rim of the cortical bone of the patella.

As shown in FIG. 12, the special tool is a concave surgical reamer 60 which can be powered electrically, pneumatically, mechanically, manually, and the like. Reamer 60 can be used to remove an appropriate amount of bone in order to create a non-planar and protruding, e.g., a convex surface, of cortical and/or cancellous bone of the bony patella which substantially matches in shape and size to the non-planar and recessed, e.g., concave undersurface of a patella implant according to the present invention.

Reamer 60 preferably includes a concave rotatable reaming member 62 whose concavity substantially equals the concavity of the patella implant undersurface. Preferably, reamer 60 further includes a solid bit 64 which protrudes from concave rotatable reaming member 62 and which is used to simultaneously drill a hole in the natural patella which will accommodate a single central peg extending from the undersurface of the implant.

Bit 64 is also used as a guide means for guiding rotatable reaming member 62 to a predetermined portion of the natural patella so that as reamer 60 is moved the natural patella is shaped to substantially match the undersurface of the patella implant.

Alternatively, bit 64 may feature a blunt end and may be used for guiding reaming member 62 through a substantially central hole pre-drilled in the natural patella.

As shown in FIG. 12, reamer 60 may feature a shaft member 68. Shaft member 68 may feature a circumferential depression 66 having two edges, 66a and 66b, for accepting an external rod (not shown) therein, the rod being connected to an external guiding device. Thus, as reamer 60 is moved, the external rod is moved along depression 66 until it is blocked by edge 66b. The extent of movement of reamer 60 is thus limited by the dimensions of the external rod and depression 66.

Alternatively, as shown in FIG. 13, reamer 60 may include two circumferential extensions, 76a and 76b, the extensions being connected to shaft member 68. Thus, as reamer 60 is moved, the external rod is moved between extensions 76a and 76b until it is blocked by extension 76b. The extent of movement of reamer 60 is thus limited by the dimensions of the external rod and the distance between extensions 76a and 76b.

Circumferential extensions 76a and 76b may be movable along shaft member 68, such that the specific location of extensions 76a and 76b and the distance between the extensions may be adapted to a specific patient. Rotatable reaming member 62 may feature a flattened central portion or any other shape substantially matching to the undersurface of the patella implant. Furthermore, reaming member 62 may feature any shape which provides enhanced bonding between the natural patella and the undersurface of the patella implant, e.g., concentric elevations 63 which will form concentric grooves in the natural patella.

Figure 14:
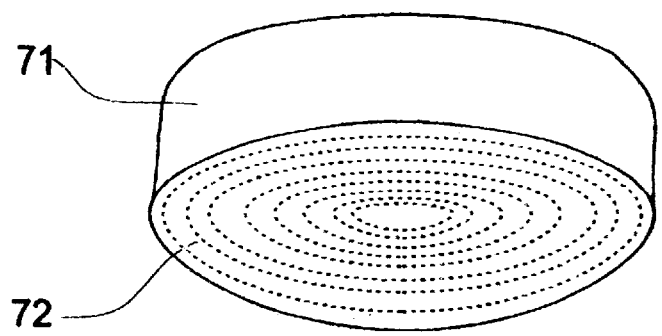
FIG. 14 illustrates one embodiment of a method according to the present invention.

Rotatable reaming member 62 may feature any suitable diameter. The diameter of reaming member 62 may approximately correspond to the diameter of the natural patella, having a diameter of between about 28 millimeters and about 44 millimeters. Thus, as shown in FIG. 14, the natural patella 71 may be shaped using reamer 60 so as to accept a patella implant of a substantially equal diameter.

Alternatively, the diameter of reaming member 62 may be smaller than the diameter of the natural patella. Thus, as shown in FIGS. 15 and 16, the natural patella 72 may be shaped using reamer 60 so as to accept a patella implant 73 of a substantially smaller diameter. Such configuration makes it possible to partly intrude patella implant 73 into the natural patella.

Preferably, the patella implant features a cylindrical circumferential facet (FIGS. 3, 6 and 13) or a conical circumferential facet (FIGS. 11, 15 and 16). When using a conical circumferential facet, the angle of the cone is preferably about 5° (FIG. 15). A conical circumferential facet may be used for facilitating the attachment of the patella implant to the remaining portion of the natural patella by means of press fitting or other fixation techniques.

Preferably, fixation of the prosthetic patella implant to the natural patella is further effected by means of a bonding material or other chemical, physical or biological adhesives and by biological reactions, such as bone ingrowth into the surface, preferably using the pegs which substantially fit into their respective holes in the prepared bone surface.

When using a patella implant with a plurality of pegs 40, their respective holes may be drilled independently by using a conventional drill, e.g., following the step of reshaping the natural patella by reamer 60.

Referring again to FIG. 1, clinical experience over 25 years has proven that tibial component 16 of total knee implants have longer longevity when fixation in the tibia 12 is enhanced with an anchoring stem 22.

Numerous designs of stem 22 are based on various mechanical concepts. These include, for example, stems which are cylindrical or rectangular and stems having a T shape in cross section. Such stems are disclosed, for example, in U.S. Pat. Nos. U.S. Pat. Nos. 4,550,448; 4,653,488; 4,298,992; 4,834,756; 4,944,756; 5,035,700 and 5,192,324.

Figure 17:
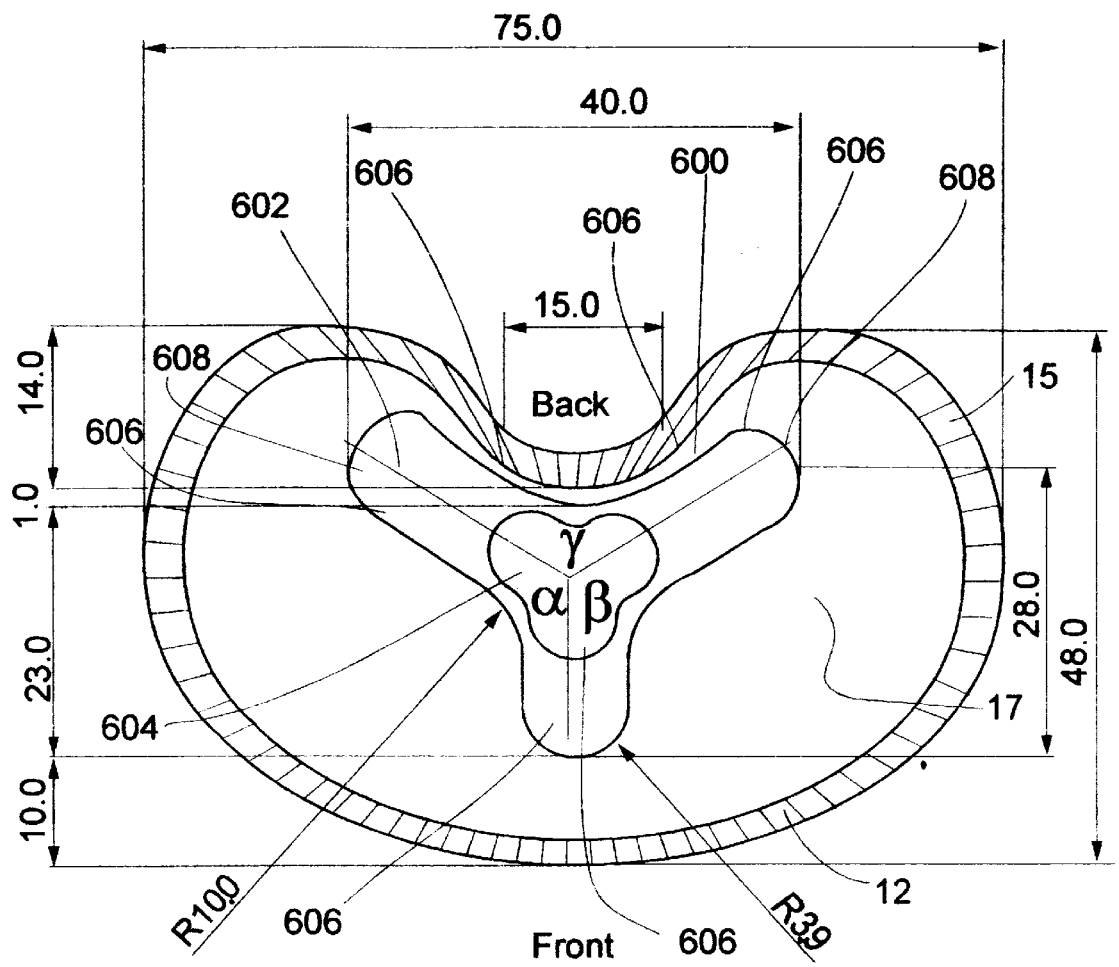
FIG. 17 is a cross sectional view of an anchoring stem according to the present invention when implemented in a tibia, preferred sizes for a medium size stem are indicated.

However, as best seen in FIG. 17, the tibial bone 12 is structurally composed of two types of bone— circumferential compact bone 15 and central trabecullar bone 17. The mechanical strength of the bone for compressive and tensile forces is provided mainly by the circumferential compact bone 15.

Tibial component 16 is placed upon a reshaped planar surface 13 (best seen in FIG. 2) of tibia 12 and most commonly it is fixed thereat with bone cement or other adhesive. Fixation is further enhanced by an anchoring stem 22 placed in a cut formed inside the bone, which is expected to transfer loads circumferentially to the compact bony walls 15 of tibia 12.

Cylindrical, rectangular or T shaped stems, as for example described in U.S. Pat. Nos. U.S. Pat. Nos. 4,550,448; 4,653,488; 4,298,992, 4,834,756; 4,944,756; 5,035,700 and 5,192,324 are inferior in transferring loads circumferentially to the compact bony walls 15 of tibia 12 since such designs are on the average located farther away from the compact bony walls 15.

As further shown in FIGS. 1 and 17, according to the present invention a tibial prosthetic component to be used in partial or total knee replacement procedures is provided comprising a tibial end-like part, which as shown in FIG. 1, may include a plastic upper plate 18 and a metal back 20, and an anchoring stem 600 having a proximal end 602 which is connected to or integrally formed with the tibial end-like part. Anchoring stem 600 further has a distal end 604. Anchoring stem 600 features three longitudinal extensions 606 extending substantially from proximal end 602 to substantially distal end 604 and forming angles $\alpha, \beta$ and $\gamma$ therebetween in a range of 105°–150°, such that, when anchoring stem 600 is inserted into a cut in a reshaped tibial bone of a patient, at least two of the three longitudinal extensions 606 are positioned closer to a compact wall 15 of the tibial bone, thereby load transfer between tibial prosthetic component 16 and tibia 12 is improved.

According to a prefered embodiment of the invention angles $\alpha, \beta$ and $\gamma$ formed between extensions 606 is each of about 120°. thereby substantially forming a clover leaf shape in cross section. Preferably, stem 600 is about 2.5–3.0, preferably about 2.7, times thinner at distal end 604 as compared with proximal end 602. Also preferably, ends 608 of the at least two of the three longitudinal extensions 606 are about 40 millimeters apart. Other dimensions of stem 600 for a typical medium size bone are given in millimeters in FIG. 17. For larger and smaller bones, about ±15% percents should be added to the indicated dimensions.

When inserted into tibial bone 12, clover leaf stem 600 according to the present invention, is of advantage when compared to a cylindrical, rectangular or T shaped stem, in achieving optimal stability while preserving bone stock.

As best seen in FIG. 17, clover leaf stem 600 optimally fits to the structure of tibia 12. The main body of stem 600 parallels the inclination of the posterior wall, the two backward extensions reach toward the postero-lateral and postero-medial walls and the forward extension reaches toward the anterior wall. It therefore, optimally transfers loads to the tibial walls and assures maximal resistance to rocking of the tibial implant in any plane as well as rotatory stability.

Stem 600 transfers most of the loads to the posterior part of the tibial wall. This is appropriate for the loads in positions of flexion such as climbing stairs when the rollback mechanism of motion of the knee joint transfers the contact areas more posteriorly and the peak of the stresses is very high.

Stem 600 is universal and may fit any tibial component of any available knee joint implant either with posterior cruciate ligament sacrifice or retainer.

The complex motion of the natural knee joint is mutually dictated by three main factors (i) the shape of the articulating surfaces of the trochlear grove and patella; (ii) the direction of pull of the muscles which are the movers of the knee joint; and (iii) the spatial orientation of the bones: femur, tibia and patella.

The patella articulates with the trochlear grove of the femur and is enclosed within the aponeurosis of the quadriceps muscle, formed by a complex of four long and diagonally oriented muscles. These muscles contribute to the helicoid (sinusoid) excursion of the patella on the helicoid orientation of the trochlear grove of the femur. See Frazer J B. "Anatomy of the Human Skeleton". London, Churchill, 1933.

The natural situation of knee flexion is presented in FIG. 18, which shows a natural femur bone 700 and a schematic patella 702 in different locations along the trochlear groove 704 while extending the knee. From flexion (bottom image), patella 702 ascends a helicoid (sinuous) course from between condyles 706 to the surface 708 of the medial condyle 710 and to the trochlear surface 712 of the femur. In full extension (top image), its shape fits comfortably and evenly into the upper end 714 of the trochlear groove 704. The helicoid excursion taken by the patella is emphasized by a sinusoidal line 716 crossing the five images of FIG. 18.

FIG. 19 shows the relative location of a natural patella 702 with respect to trochlear groove 704 of femur bone 700 in full extension of the knee, wherein arrow 720 indicated its line of excursion along trochlear groove 704 during extension/flexion.

Therefore, as shown in FIG. 20, further according to the present invention there is provided a femoral prosthetic component 800 to be used in partial or total knee replacement procedure.

Component 800 includes a femoral end-like part 802 formed with lateral and medial elevations 804 which simulate the lateral and medial condyles of a natural femur bone.

An interelevations groove 805 is formed between elevations 804, simulating the intercondylar groove of a natural femur bone. Femoral end-like part 802 is further formed with a helicoid groove 806 which simulate a natural trochlear grove of the natural femur bone.

Helicoid groove 806 is located in an anterior aspect 808 of femoral end-like part 802 and terminates where groove 805 originate, at a posterior aspect 810 of part 802, such that when femoral prosthetic component 800 is implanted in a patient, helicoid groove 806 dictates a patella or a patella implant of the patient to follow a helicoid route, as indicated, for example, in FIG. 19 by arrow 720.

Thus, femoral implant component 800 according to the present invention is designed to approximately simulate the anatomical shape of the femoral part of the knee joint. To this end helicoid groove 806, which is the gist of this aspect of the present invention, is provided.

Although 50 years of experience with modern orthopedic implants for human joints have proved that simulation of nature is the key for success, prior art femoral implants, as, for example described in U.S. Pat. Nos. 4,298,992, 4,950, 298; 5,047,058; 5,053,037; 5,100,408; 5,282,803; 5,514, 140; 5,354,075; 5,417,694 and 5,549,688; UK Pat. No. 2067412 and AU Pat. No. 542787, fails to reconstruct a helicoid groove to simulate the anatomical helicoid shape of the trochlear groove.

As best seen in FIG. 19, the lateral wall 722 of the anatomical trochlear groove is raised, therefore, as shown in FIG. 20, a raised lateral wall 812 is preferably provided with helicoid groove 806 of component 800 according to the present invention. In both cases, the direction of the groove is from proximal—lateral to distal—medial, dictating a helicoid route for a patella or a patella implant of a patient. Therefore, differently designed (mirror images) right knee and left knee tibial components are an essential part of the present invention.

According to a preferred embodiment of this aspect of the present invention, the length of the helicoid grove from is proximal to its distal end is 60±15 millimeters. The width of the helicoid grove is 30±10 millimeters. Whereas the depth of the helicoid grove is 5±3 millimeters. These values simulate the situation in the natural femur of individuals of different sizes.

Any of the implants according to the present invention or any part or parts thereof may be fabricated from materials known in the art, such as, for example, metal or alloy (e.g., steel), plastic, ceramic materials and composite materials. Furthermore, parts of the implants which are to be permanently engaged to natural bone may be formed suitable for bone ingrowth.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A tibial prosthetic component to be used in partial or total knee replacement procedure comprising a tibial end-like part and an anchoring stem having a proximal end being attached to said tibial end-like part, said anchoring stem further having a distal end, said anchoring stem featuring three longitudinal extensions extending substantially from said proximal end to substantially said distal end, said three longitudinal extensions forming angles therebetween in a range of 105°–150°, such that, when said stem is inserted into a cut in a reshaped tibial bone of a patient, at least two of said three longitudinal extensions are positioned closer to a compact wall of said tibial bone, thereby load transfer between the tibial prosthetic component and the tibia is improved.

2. The tibial prosthetic component of claim 1, wherein each of said angles is of about 120°, thereby substantially forming a clover leaf shape in cross section.

3. The tibial prosthetic component of claim 1, wherein said stem is about 2.5–3.0 times thinner at said distal end as compared with said proximal end.

4. The tibial prosthetic component of claim 1, wherein ends of said at least two of said three longitudinal extensions are about 40 millimeters apart.

5. The tibial prosthetic component of claim 1, wherein said tibial end-like part includes a plastic upper plate and a metal back.

* * * * *